US012649721B2

(12) United States Patent
Ding et al.

(10) Patent No.: US 12,649,721 B2
(45) Date of Patent: Jun. 9, 2026

(54) CSF1R KINASE INHIBITOR AND USE THEREOF

(71) Applicant: SHANGHAI INSTITUTE OF MATERIA MEDICA, CHINESE ACADEMY OF SCIENCES, Shanghai (CN)

(72) Inventors: Jian Ding, Shanghai (CN); Wenhu Duan, Shanghai (CN); Hua Xie, Shanghai (CN); Meiyu Geng, Shanghai (CN); Caixia Wang, Shanghai (CN); Zhengsheng Zhan, Shanghai (CN); Na Gao, Shanghai (CN); Yang Zhang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 515 days.

(21) Appl. No.: 18/027,759

(22) PCT Filed: Sep. 22, 2021

(86) PCT No.: PCT/CN2021/119663
§ 371 (c)(1),
(2) Date: Mar. 22, 2023

(87) PCT Pub. No.: WO2022/063134
PCT Pub. Date: Mar. 31, 2022

(65) Prior Publication Data

US 2023/0382871 A1 Nov. 30, 2023

(30) Foreign Application Priority Data

Sep. 23, 2020 (CN) ........................ 202011007689.2

(51) Int. Cl.
*C07D 231/56* (2006.01)
*A61K 39/00* (2006.01)
(Continued)

(52) U.S. Cl.
CPC ............ *C07D 231/56* (2013.01); *A61P 35/00* (2018.01); *C07K 16/2818* (2013.01); *C07K 16/2827* (2013.01); *A61K 2039/505* (2013.01)

(58) Field of Classification Search
CPC .............. C07D 231/56; C07K 16/2818; A61K 2039/505; A61P 35/00
(Continued)

(56) References Cited

U.S. PATENT DOCUMENTS 9,914,707 B2 * 3/2018 Duan et al. .......... C07D 231/56
11,591,328 B2 2/2023 Liu et al.
(Continued)

FOREIGN PATENT DOCUMENTS

EP 2 439 195 A1 4/2012
WO WO 2007/005668 A2 1/2007
WO WO 2019/228252 A1 12/2019

OTHER PUBLICATIONS

Di Tacchio M, et al . . . Tumor vessel normalization, immunostimulatory reprogramming, and improved survival in glioblastoma with combined inhibition of PD-1, angiopoietin-2, and VEGF. Cancer immunology research. Dec. 1, 2019;7(12):1910-27. (Year: 2019).*
(Continued)

*Primary Examiner* — Jeffrey S Lundgren
*Assistant Examiner* — Heather Dahlin
(74) *Attorney, Agent, or Firm* — Leydig, Voit & Mayer, Ltd.

(57) ABSTRACT

Provided is the use of a CSF1R kinase inhibitor compound or a pharmaceutically acceptable salt thereof in the preparation of drugs for treating diseases related to the CSF1R
(Continued)

kinase signal transduction pathway or drugs for regulating immunization.

2 Claims, 3 Drawing Sheets

(51) Int. Cl.
*A61P 35/00* (2006.01)
*C07K 16/28* (2006.01)

(58) Field of Classification Search
USPC .......................................................... 514/406
See application file for complete search history.

(56) References Cited

U.S. PATENT DOCUMENTS

| | | | |
|---|---|---|---|
| 2007/0054903 | A1 | 3/2007 | Kim et al. |
| 2009/0054411 | A1 | 2/2009 | Cook et al. |
| 2010/0130490 | A1 | 5/2010 | Ng et al. |
| 2017/0066723 | A1 | 3/2017 | Duan et al. |
| 2017/0327506 | A1 | 11/2017 | Buffa et al. |
| 2020/0253973 | A1 | 8/2020 | Flynn et al. |

OTHER PUBLICATIONS

Ciciola P, Cascetta P, Bianco C, Formisano L, Bianco R. Combining immune checkpoint inhibitors with anti-angiogenic agents. Journal of clinical medicine. Mar. 3, 2020;9(3):675. (Year: 2020).*

Peyraud et al., "CSF-1R Inhibitor Development: Current Clinical Status", *Current Oncology Reports,* 19:70, pp. 1-10 (2017).

Xun et al., "Small-Molecule CFR1R Inhibitors as Anticancer Agents", *Current Medicinal Chemistry,* 27: 3944-3966 (2020).

Lv et al., "Discovery of a New Series of Naphthamides as Potent VEGFR-2 Kinase Inhibitors", *ASC Medicinal Chemistry Letters,* 5: 592-597 (2014).

Qin et al., "Recent advances on anti-angiogenesis receptor tyrosine kinase inhibitors in cancer therapy", *Journal of Hematology & Oncology,* 12: 27, pp. 1-11 (2019).

China National Intellectual Property Administration, International Search Report and Written Opinion issued in International Patent Application No. PCT/CN2021/119663, mailed on Dec. 22, 2021.

* cited by examiner

CSF1R KINASE INHIBITOR AND USE THEREOF

CROSS-REFERENCE TO RELATED APPLICATIONS

The present application is the U.S. National Stage of International Patent Application No. PCT/CN2021/119663, filed Sep. 22, 2021, which claims priority to Chinese Patent Application No. 202011007689.2 filed on Sep. 23, 2020, which are each incorporated herein by reference in its entirety for all purposes.

TECHNICAL FIELD

The present application generally pertains to the medical field. Specifically, the present application relates to a CSF1R kinase inhibitor and its use for the treatment of a disease associated with the CSF1R kinase signaling pathway or for an improvement of a tumor immunosuppressive status (as a CSF1R kinase inhibitor medicament).

BACKGROUND OF THE INVENTION

Tumor microenvironment, which functionally act in its entirety and is inseparable, plays an important role in tumor progression. Numerous stromal cells in the microenvironment, such as tumor-associated macrophages (TAMs), dendritic cells (DC), regulatory T cells (Treg), fibroblasts, or killer T cells, advance tumor progression by interacting with tumor cells.

Among them, tumor-associated macrophages (TAMs) are important microenvironmental stromal cells. In some tumor tissues, the proportion of macrophages can be up to 50%. Macrophages may constitute 30% or more of the tumor weight in a brain glioma. Macrophages are a class of the most important antigen-presenting cells in the body, exist at all stages of tumor progression, and are called tumor-associated macrophages (TAMs). Classical activated macrophages (M1 type) are widely involved in intrinsic immunity and adaptive immunity in the body, play an antigen presenting role, and have significant killing and inhibiting effects on tumors. Alternative activated macrophages (M2 type) act in an immunosuppressive way, and play an important role in facilitating growth angiogenesis, invasion and metastasis of tumors. Macrophage colony stimulating factor (CSF1) is a classic pro-tumor cytokine. It recruits macrophages to tumor areas and facilitates the interaction of tumor cells with macrophages, which results in the release of various pro-tumor growth factors (such as VEGF, or matrix metalloproteinases) in the microenvironment, thereby facilitating tumor growth and metastasis. CSF1 exerts its biological effect by binding to its unique cell surface receptor, CSF1R. Upon binding to its receptor CSF1R, CSF1 triggers a signal cascade that functions by activating multiple downstream signaling pathways. Studies have shown that CSF1 and CSF1R have abnormally elevated levels in a variety of malignancies, and are closely related to tumorigenesis, progression, and poor prognosis. Therefore, CSF1R has become a critical target for managing tumor-associated macrophages in the tumor microenvironment, and the development of small-molecule inhibitors of CSF1R has received increasing attention.

Several small-molecule CSF1R inhibitors are currently in clinical trial phases, and among them, more promising selective CSF1R inhibitors include Pexidartinib (also known as PLX3397) and BLZ945. PLX3397 was approved for the treatment of tenosynovial giant cell tumor (TGCT) in August 2019. TGCT is a benign soft tissue tumor caused by overexpression of CSF1. PLX3397, as an inhibitor of CSF1R, can reduce the number of TAMs in tumors by blocking the CSF1/CSF1R signaling pathway and repolarize the TAMs, resulting in a reduction in the number of M2-type TAMs. CSF1R is demonstrated to be a highly potential target for tumor therapy. However, PLX3397 has significant toxic side effects, and had a black box warning in its drug label, indicating that PLX3397 has the risk of serious and potentially fatal liver injury. In addition, marketed drugs, such as Pazopanib, Imatinib or Sunitinib, have been reported to have CSF1R inhibitory activity, but they are all generic inhibitors. No clinical indication has been identified for these drugs via targeting CSF1R. Furthermore, no highly selective CSF1R inhibitor has been approved for the treatment of tumors. Therefore, the development of safe and effective drugs targeting CSF1R in treating prevalent solid tumors has not been successful. Therefore, further research is needed to meet clinical needs.

The most important progress in cancer treatment in the past decade involves immune checkpoint drugs represented by anti-CTLA-4 antibodies and anti-PD-1/anti-PD-L1 antibodies. Such immunotherapies can repair anti-tumor immunity, thereby reversing immune escape of tumors and facilitating tumor cell death. The indications of such immunotherapies have been being expanded, and many of previous standard therapies have been replaced. However, it cannot be ignored that the immune system may be over-activated, resulting in an increase of immune-related adverse events. It is reported that up to 60% of patients treated with Yervoy, an anti-CTLA-4 antibody, would experience immune-related adverse events, of which 10-30% were severe (grade 3-4) immune-related adverse events. The adverse events were dose-dependent. Approximately 10% of patients treated with anti-PD-1 antibodies would experience ≥grade 3 immune-related adverse events, including fatigue, headache, arthralgia, rash, pruritus, pneumonia, diarrhea and/or colitis, hepatitis and endocrine diseases. The combination administration of an anti-CTLA-4 antibody with an anti-PD-1 antibody increases the incidence and severity of immune-related adverse events. Some of the patients treated with Bavencio, an anti-PD-L1 antibody, experienced an infusion-related response predominantly of grade 1-3 severity. Generally, these adverse effects are dose-related. Lowering the dose can reduce or alleviate adverse effects, while impacting the anti-tumor effect. Therefore, how to enhance the anti-tumor effects of immune checkpoint drugs or strengthen their anti-tumor effects at low doses is an urgent technical problem to be solved.

BRIEF SUMMARY OF THE INVENTION

Chinese Patent No. 201410062209.0 (also published as CN 104860885 B, which is incorporated herein by reference in its entirety for all purposes) discloses compounds represented by formula (A), especially compounds having the structure of formula (I), (A)

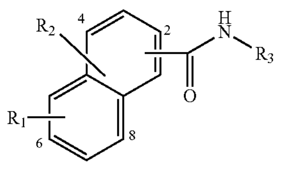

-continued (B)

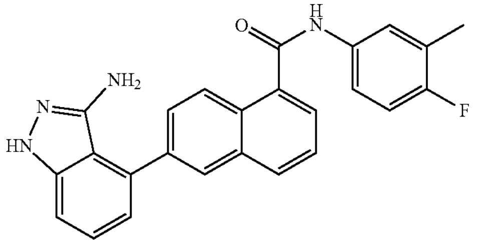

In CN 104860885 B, these compounds are reported as VEGFR inhibitors having excellent activities and being capable of inhibiting tumor angiogenesis. The inventors of the present application further studied the compound of formula (I) as a representative, and found that such compounds were also potent inhibitors of CSF1R kinase, and were capable of inhibiting tumor-associated macrophages, activating $CD8^+$ T cells, antagonizing tumor immunosuppressive microenvironments, and enhancing the anti-tumor efficacy of immune checkpoint drugs. The compounds exhibited significantly therapeutic efficacy in subcutaneous xenografts tumor models of multiple human or murine cells, and brain in situ xenograft models.

Current clinical studies have shown that although selective CSF1R inhibitors can act on TAMs to exert anti-tumor effects, a mono-therapy cannot strongly inhibit tumor growth. Therefore, combination therapies are effective strategies to improve the anti-tumor effect of such inhibitors. Moreover, a defect of drugs targeting VEGF/VEGFR lies in short duration of pharmaceutical effects. One important reason is that TAMs in the tumor microenvironment generate angiogenic factors and enzymes, such as VEGF, to facilitate tumor neovascularization, thereby significantly decreasing the therapeutic effects of drugs targeting VEGF/VEGFR. On the basis of this discovery, several studies have shown that drugs targeting VEGF/VEGFR and drugs targeting CSF1R, when used in combination, can effectively and synergistically exert anti-tumor effects. Thus, development of selective inhibitors targeting both VEGFR and CSF1R is of great value. Such inhibitors not only have the dual effects of inhibiting tumor angiogenesis and inhibiting the function of TAMs in the tumor microenvironment, but also can effectively avoid decreased efficacy of drugs targeting VEGFR caused by TAMs in the microenvironment. Therefore, development of VEGFR/CSF1R dual-target inhibitors is expected to provide a new therapeutic strategy for tumor therapy.

In general, the present application provides various applications of a compound represented by formula (A) or a pharmaceutically acceptable salt thereof as a CSF1R kinase inhibitor, including use in medicament manufacture, methods of treating diseases, pharmaceutical compositions and use thereof, which are described below in various aspects.

The compounds represented by formula (A) of the present application are:

(A)

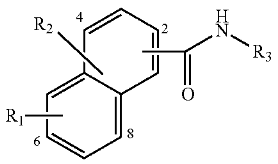

wherein:

$R_1$ is at any one of positions 5-8 on the naphthalene ring and has one of the following structures:

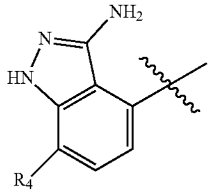
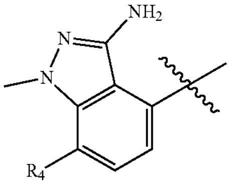
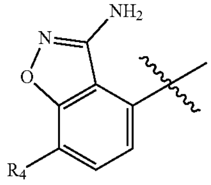
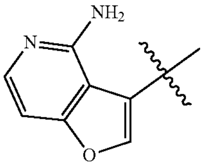
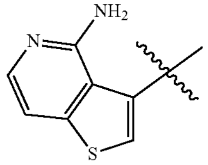
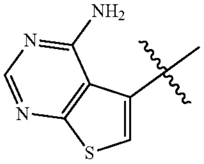
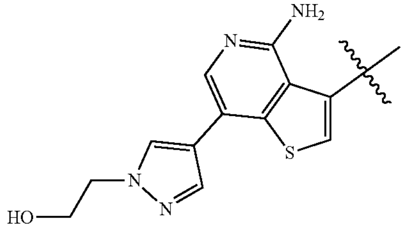
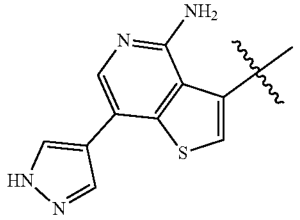
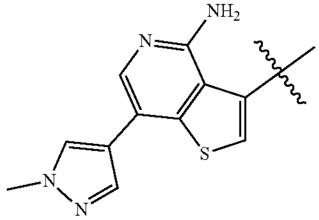, $R_4$ is selected from the group consisting of hydrogen, halogen, a $C_1$-$C_3$ alkyl and a $C_1$-$C_3$ alkoxy, the group

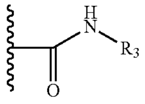

is at any one of positions 1 to 4 on the naphthalene ring; and

R3 is selected from the group consisting of hydrogen, a C1-C6 alkyl, a C3-C6 cycloalkyl, a substituted or unsubstituted phenyl, and a substituted or unsubstituted 5-10 membered heteroaryl containing 1 to 5 heteroatoms selected from the group consisting of N, O, and S, and where R3 is a substituted group, R3 has 1 to 3 substituents each of which is independently selected from the group consisting of a C1-C3 alkyl, a C1-C3 alkoxy, a haloC1-C3 alkyl, a halo$C_1$-$C_3$ alkoxy, hydroxy, amino, nitro, and halogen; and R2 is hydrogen or halogen and is at any one of positions 1 to 8 on the naphthalene ring except for the positions that R1 and the group

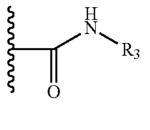

are at.

In some embodiments of formula (A), R3 is selected from the group consisting of hydrogen, a C1-C3 alkyl, a C3-C6 cycloalkyl, a substituted or unsubstituted phenyl and a substituted or unsubstituted 5-6 membered heteroaryl containing 1 to 3 heteroatoms selected from the group consisting of N, O and S, and where R3 is a substituted group, R3 has 1 to 3 substituents, each of which is independently selected from the group consisting of a C1-C3 alkyl, methoxy, trifluoromethyl, trifluoromethoxy, hydroxy, amino, nitro, F, Cl and Br; and R2 is hydrogen, F, Cl or Br.

In some embodiments of formula (A), R4 is selected from the group consisting of hydrogen, F, Cl, Br, methyl and methoxy.

In some embodiments, the compound represented by formula (A) is a compound represented by formula (B):

(B)

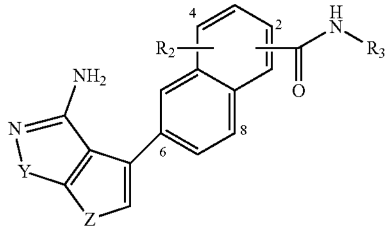

wherein:

the group

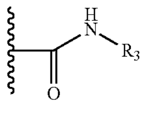

is at any one of positions 1 to 4 on the naphthalene ring;

$R_3$ is selected from the group consisting of hydrogen, a $C_1$-$C_6$ alkyl, a $C_3$-$C_6$ cycloalkyl, a substituted or unsubstituted phenyl, and a substituted or unsubstituted 5-10 membered heteroaryl containing 1 to 5 heteroatoms selected from the group consisting of N, O, and S, and where $R_3$ is a substituted group, $R_3$ has 1 to 3 substituents, each of which is independently selected from the group consisting of a $C_1$-$C_3$ alkyl, a $C_1$-$C_3$ alkoxy, a halo$C_1$-$C_3$ alkyl, a halo$C_1$-$C_3$ alkoxy, hydroxy, amino, nitro, and halogen;

$R_2$ is hydrogen or halogen and is at any one of positions 1 to 8 on the naphthalene ring except for the positions that $R_1$ and the group

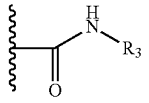

are at;

Z is $C(R_5)$═CH, S or O;

Y is NH, NMe, O, CH═$C(R_6)$ or CH═N;

$R_5$ is selected from the group consisting of hydrogen, halogen, a $C_1$-$C_3$ alkyl and a $C_1$-$C_3$ alkoxy;

$R_6$ is selected from the group consisting of hydrogen, pyrazolyl, pyrazolyl substituted with a $C_1$-$C_3$ alkyl, and pyrazolyl substituted with a hydroxy$C_1$-$C_3$ alkyl.

In some embodiments of formula (B), $R_5$ is selected from the group consisting of hydrogen, F, Cl, Br, methyl and methoxy; and $R_6$ is selected from the group consisting of hydrogen, pyrazolyl, pyrazolyl substituted with methyl, and pyrazolyl substituted with hydroxyethyl.

In some embodiments, the compound represented by formula (A) is a compound represented by formula (C), (D), (E) or (F):

(C)

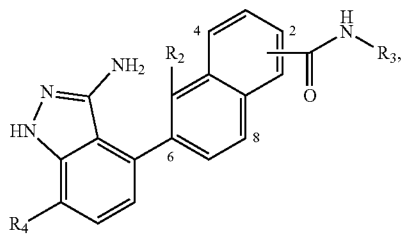

(D)

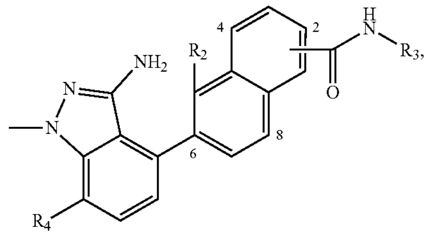

(E)

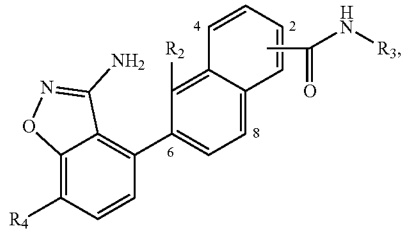

(F)

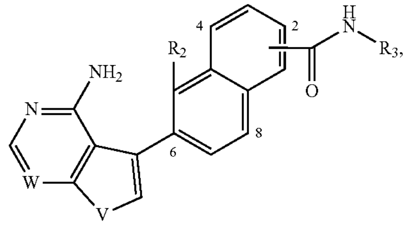

wherein:

the group

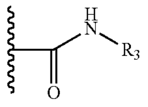

is at position 1 or 2 on the naphthalene ring;

$R_3$ is selected from the group consisting of hydrogen, a $C_1$-$C_6$ alkyl, a $C_3$-$C_6$ cycloalkyl, a substituted or unsubstituted phenyl, and a substituted or unsubstituted 5-10 membered heteroaryl containing 1 to 5 heteroatoms selected from the group consisting of N, O, and S, and where $R_3$ is a substituted group, $R_3$ has 1 to 3 substituents each of which is independently selected from the group consisting of a $C_1$-$C_3$ alkyl, a $C_1$-$C_3$ alkoxy, a halo$C_1$-$C_3$ alkyl, a halo$C_1$-$C_3$ alkoxy, hydroxy, amino, nitro, and halogen;

$R_2$ is hydrogen or halogen and is at any one of positions 1 to 8 on the naphthalene ring except for the positions that $R_1$ and the group

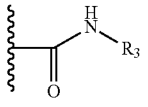

are at.

$R_4$ is selected from the group consisting of hydrogen, halogen, a $C_1$-$C_3$ alkyl and a $C_1$-$C_3$ alkoxy;

V is S or O;

W is N or $C(R_7)$;

$R_7$ is selected from the group consisting of hydrogen, pyrazolyl, pyrazolyl substituted with a $C_1$-$C_3$ alkyl, and pyrazolyl substituted with a hydroxy$C_1$-$C_3$ alkyl.

In some embodiments of formula (C), (D), (E), or (F), $R_4$ is selected from the group consisting of hydrogen, F, Cl, Br, methyl and methoxy; and $R_7$ is selected from the group consisting of hydrogen, pyrazolyl, pyrazolyl substituted with methyl, and pyrazolyl substituted with hydroxyethyl.

In a particular embodiment, the compound represented by formula (A) is a compound represented by formula (I) (also referred to herein as "Compound I", as a leading compound in the present application):

(I)

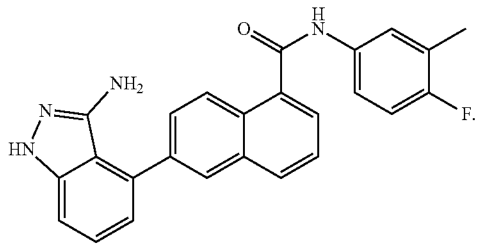

In one aspect, the present application provides use of compounds represented by formulae (A) to (F), or pharmaceutically acceptable salts thereof, in particular Compound I or a pharmaceutically acceptable salt thereof, in the manufacture of a medicament for the treatment of a disease associated with the CSF1R kinase signaling pathway (a CSF1R kinase inhibitor medicament).

The disease associated with the CSF1R kinase signaling pathway described herein includes a cancer or tumor, hyperplasia, an immune disorder, and an inflammatory disorder. In some embodiments, the disease is a cancer or tumor. In some embodiments, the cancer or tumor is a CSF1/CSF1R-dependent cancer or tumor or a TAMs-enriched tumor. In some further particular embodiments, the CSF1/CSF1R-dependent cancer or tumor includes a CSF1/CSF1R-dependent leukemia and tenosynovial giant cell tumor. The TAMs-enriched tumor includes, but is not limited to, a glioma, a metastatic brain tumor, and a colorectal cancer.

In another aspect, the present application provides use of compounds represented by formulae (A) to (F), or pharmaceutically acceptable salts thereof, in particular Compound I or a pharmaceutically acceptable salt thereof, in the manufacture of a medicament for immunoregulation. In some embodiments, the immunoregulation is immunopotentiation. In some embodiments, the immunopotentiation is an improvement of a tumor immunosuppressive state. In some further particular embodiments, the improvement of the tumor immunosuppressive state is inhibiting the survival of M2-biased macrophages, reversing an M2-biased polarization phenotype of macrophages and the inhibitory effect of the M2-biased polarization phenotype of macrophages on $CD8^+$ T cells, and/or rebuilding a tumor immune microenvironment.

In another aspect, the present application provides use of compounds represented by formulae (A) to (F), or pharmaceutically acceptable salts thereof, in particular Compound I or a pharmaceutically acceptable salt thereof, in the manufacture of a medicament for inhibiting proliferation of M2-biased macrophages.

In another aspect, the present application provides use of compounds represented by formulae (A) to (F), or pharmaceutically acceptable salts thereof, in particular Compound I or a pharmaceutically acceptable salt thereof, in the manufacture of a medicament for the treatment or inhibition of a tumor insensitive to an immune checkpoint drug. In some embodiments, the immune checkpoint drug is an anti-PD-1 antibody or an anti-PD-L1 antibody. In some embodiments, the tumor includes, but is not limited to, glioma, brain metastases, and colorectal cancer.

In another aspect, the present application provides use of compounds represented by formulae (A) to (F), or pharmaceutically acceptable salts thereof, in particular Compound I or a pharmaceutically acceptable salt thereof, in the manufacture of a medicament for enhancing the anti-tumor efficacy of an immune checkpoint drug. In some embodiments, the immune checkpoint drug is an anti-PD-1 antibody or an anti-PD-L1 antibody. In some embodiments, the tumor includes, but is not limited to, a glioma, a metastatic brain tumor, and a colorectal cancer.

In another aspect, the present invention provides use of compounds represented by formulae (A) to (F), or pharmaceutically acceptable salts thereof, in particular Compound I or a pharmaceutically acceptable salt thereof, in the manufacture of an anti-tumor medicament for use in combination with an immune checkpoint drug. In some embodiments, the immune checkpoint drug is an anti-PD-1 antibody or an anti-PD-L1 antibody. In some embodiments, the tumor includes, but is not limited to, a glioma, a metastatic brain tumor, and a colorectal cancer.

Further, in the use described above, the medicament comprises a therapeutically effective amount of compounds represented by formulae (A) to (F), or pharmaceutically acceptable salts thereof, in particular Compound I, or a pharmaceutically acceptable salt thereof, and optionally, a pharmaceutically acceptable excipient or carrier.

The administration mode of the medicament of the present application is not particularly limited. Representative administration modes include, but are not limited to, oral, intratumoral, rectal, parenteral (intravenous, intramuscular or subcutaneous) and topical administration. Accordingly, the medicament of the present application can be formulated into a variety of clinically acceptable formulations, including formulations for oral administration, injection, topical administration or external application.

The medicament of the present application may be used clinically alone or in combination with an additional therapeutic agent. In some embodiments, the additional therapeutic agent is an anti-tumor drug or an immunomodulator. In some embodiments, the medicament of the present application may be used in combination with an immune checkpoint drug. In some embodiments, the immune checkpoint drug includes an anti-PD-1 antibody and an anti-PD-L1 antibody. For ease of clinical use, compounds represented by formulae (A) to (F), or pharmaceutically acceptable salts thereof, in particular Compound I, or a pharmaceutically acceptable salt thereof, may be combined with an additional therapeutic agent to prepare a compound medicament or pharmaceutical combination product. In some embodiments, the additional therapeutic agent is an anti-tumor drug or an immunomodulator. In some particular embodiments, the additional therapeutic agent is an immune checkpoint drug. In some further particular embodiments, the immune checkpoint drug is an anti-PD-1 antibody or an anti-PD-L1 antibody.

In another aspect, the present application provides a method of using the medicament comprising administering to a subject in need of treatment a therapeutically effective amount of compounds represented by formulae (A) to (F), or pharmaceutically acceptable salts thereof, in particular Compound I, or a pharmaceutically acceptable salt thereof. The subject may be a mammal, such as a human.

In another aspect, the present application provides a method of treating a disease associated with the CSF1R kinase signaling pathway, comprising administering to a subject in need of the treatment a therapeutically effective amount of compounds represented by formulae (A) to (F), or pharmaceutically acceptable salts thereof, in particular Compound I, or a pharmaceutically acceptable salt thereof. The subject may be a mammal, such as a human. The disease associated with the CSF1R kinase signaling pathway described herein includes a cancer or tumor, hyperplasia, an immune disorder, and an inflammatory disorder. In some embodiments, the disease is a cancer or tumor. In some embodiments, the cancer or tumor is a CSF1/CSF1R-dependent cancer or tumor or a TAMs-enriched tumor. In some further particular embodiments, the CSF1/CSF1R-dependent cancer or tumor includes a CSF1/CSF1R-dependent leukemia and tenosynovial giant cell tumor. The TAMs-enriched tumor includes, but is not limited to, a glioma, a metastatic brain tumor, and a colorectal cancer.

In another aspect, the application provides a method of immunoregulation, comprising administering to a subject in need thereof a therapeutically effective amount of compounds represented by formulae (A) to (F), or pharmaceutically acceptable salts thereof, in particular Compound I, or a pharmaceutically acceptable salt thereof. The subject may be a mammal, such as a human. In some embodiments, the immunoregulation is immunopotentiation. In some embodiments, the immunopotentiation is an improvement of a tumor immunosuppressive state. In some further particular embodiments, the improvement of the tumor immunosuppressive state is inhibiting the survival of M2-biased macrophages, reversing an M2-biased polarization phenotype of macrophages and the inhibitory effect of the M2-biased polarization phenotype of macrophages on $CD8^+$ T cells, and/or rebuilding a tumor immune microenvironment.

In another aspect, the present application provides a method of treating or inhibiting a tumor insensitive to an immune checkpoint drug, comprising administering to a subject in need of treatment or inhibition of a tumor insensitive to an immune checkpoint drug a therapeutically effective amount of compounds represented by formulae (A) to (F), or pharmaceutically acceptable salts thereof, in particular Compound I, or a pharmaceutically acceptable salt thereof. The subject may be a mammal, such as a human. In some embodiments, the immune checkpoint drug is an anti-PD-1 antibody or an anti-PD-L1 antibody. In some embodiments, the tumor includes, but is not limited to, a glioma, a metastatic brain tumor, or a colorectal cancer.

In another aspect, the present application provides a method of enhancing the anti-tumor efficacy of an immune checkpoint drug, comprising administering to a subject who is receiving or going to receive an anti-tumor treatment with an immune checkpoint drug a therapeutically effective amount of compounds represented by formulae (A) to (F), or pharmaceutically acceptable salts thereof, in particular Compound I, or a pharmaceutically acceptable salt thereof. The subject may be a mammal, such as a human. In some embodiments, the immune checkpoint drug is an anti-PD-1 antibody or an anti-PD-L1 antibody.

In another aspect, the present application provides a method of treating or inhibiting a tumor, comprising the step of administering a therapeutically effective amount of compounds represented by formulae (A) to (F), or pharmaceutically acceptable salts thereof, in particular Compound I, or a pharmaceutically acceptable salt thereof, in combination with an immune checkpoint drug to a subject in need of treatment or inhibition of the tumor. The subject may be a mammal, such as a human. In some embodiments, the immune checkpoint drug is an anti-PD-1 antibody or an anti-PD-L1 antibody. In some embodiments, the tumor includes, but is not limited to, a glioma, a metastatic brain tumor, or a colorectal cancer.

It is to be understood that the combination administration described herein includes any suitable way of administering drugs in combination, including, but not limited to, formulating two or more pharmaceutical active ingredients into a single pharmaceutical composition for administration, or formulating two or more pharmaceutical active ingredients separately into separate pharmaceutical compositions for simultaneous or sequential administration.

In another aspect, the present application provides compounds represented by formulae (A) to (F), or pharmaceutically acceptable salts thereof, in particular Compound I, or a pharmaceutically acceptable salt thereof, for use as a CSF1R kinase inhibitor.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for use in treating a disease associated with the CSF1R kinase signaling pathway in a subject. The disease associated with the CSF1R kinase signaling pathway described herein includes a cancer or tumor, hyperplasia, an immune disorder, and an inflammatory disorder. In some embodiments, the disease is a cancer or tumor. In some embodiments, the cancer or tumor is a CSF1/CSF1R-dependent cancer or tumor or a TAMs-enriched tumor. In some further particular embodiments, the CSF1/CSF1R-dependent cancer or tumor includes a CSF1/CSF1R-dependent leukemia and tenosynovial giant cell tumor. The TAMs-enriched tumor includes, but is not limited to, a glioma, a metastatic brain tumor, and a colorectal cancer.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for use in immunoregulation. In some embodiments, the immunoregulation is immunopotentiation. In some embodiments, the immunopotentiation is an improvement of a tumor immunosuppressive state. In some further particular embodiments, the improvement of the tumor immunosuppressive state is inhibiting the survival of M2-biased macrophages, reversing an M2-biased polarization phenotype of macrophages and the inhibitory effect of the M2-biased polarization phenotype of macrophages on $CD8^+$ T cells, and/or rebuilding a tumor immune microenvironment.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for inhibiting proliferation of macrophages with an M2-biased polarization phenotype.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for the treatment or inhibition of a tumor insensitive to an immune checkpoint drug. In some embodiments, the immune checkpoint drug is an anti-PD-1 antibody or an anti-PD-L1 antibody. In some embodiments, the tumor includes, but is not limited to, a glioma, a metastatic brain tumor, or a colorectal cancer.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for enhancing the anti-tumor efficacy of an immune checkpoint drug. In some embodiments, the immune checkpoint drug is an anti-PD-1 antibody or an anti-PD-L1 antibody. In some embodiments, the tumor includes, but is not limited to, a glioma, a metastatic brain tumor, or a colorectal cancer.

In another aspect, the present application provides a pharmaceutical composition comprising a therapeutically effective amount of compounds represented by formulae (A) to (F), or pharmaceutically acceptable salts thereof, in particular Compound I, or a pharmaceutically acceptable salt thereof, for use in combination with an immune checkpoint drug to treat or inhibit a tumor in a subject. The subject may be a mammal, such as a human. In some embodiments, the immune checkpoint drug is preferably an anti-PD-1 antibody or an anti-PD-L1 antibody. In some embodiments, the tumor includes, but is not limited to, a glioma, a metastatic brain tumor, or a colorectal cancer.

In another aspect, the present application provides a compound medicament or pharmaceutical combination product comprising a therapeutically effective amount of compounds represented by formulae (A) to (F), or pharmaceutically acceptable salts thereof, in particular Compound I, or a pharmaceutically acceptable salt thereof, and an additional therapeutic agent, for treating or inhibiting a disease associated with the CSF1R kinase signaling pathway in a subject.

The disease associated with the CSF1R kinase signaling pathway described herein includes a cancer or tumor, hyperplasia, an immune disorder, and an inflammatory disorder. In some embodiments, the disease is a cancer or tumor. In some embodiments, the cancer or tumor is a CSF1/CSF1R-dependent cancer or tumor or a TAMs-enriched tumor. In some further particular embodiments, the CSF1/CSF1R-dependent cancer or tumor includes a CSF1/CSF1R-dependent leukemia and tenosynovial giant cell tumor. The TAMs-enriched tumor includes, but is not limited to, a glioma, a metastatic brain tumor, and a colorectal cancer.

In some embodiments, the additional therapeutic agent is an anti-tumor drug or an immunomodulator. In some embodiments, the additional therapeutic agent is an immune checkpoint drug. In some embodiments, the immune checkpoint drug is an anti-PD-1 antibody or an anti-PD-L1 antibody.

It is to be understood that the product form of a pharmaceutical combination product herein includes not only a single pharmaceutical composition formulated with two or more pharmaceutical active ingredients, but also a kit. For example, two or more pharmaceutical active ingredients are formulated separately as separate pharmaceutical compositions, and are physically separated with respect to each other in a product.

As used herein, "a therapeutically effective amount" as used herein refers to a pharmaceutically effective administration dose, i.e., an amount of an active compound sufficient to significantly ameliorate a condition without causing severe side effects. For a person of 60 kg body weight, the daily dose is generally 0.01-2000 mg, preferably 1-500 mg, or 5-500 mg, or 5-200 mg. Exemplary effective administration doses are, for example, 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 250 mg, 300 mg, 350 mg, 400 mg, 450 mg, or 500 mg. Preferably, the above daily dose is based on compounds represented by formulae (A) to (F), in particular Compound I. The medicament can be administered in a single dose once a day, in multiple doses in a day, or at intervals. The dosage of an anti-PD-1 antibody, or an anti-PD-L1 antibody depends on the specific type of antibody, the type of cancer, and the stage of cancer. Administration dose for each time can be 0.5 mg/kg-30 mg/kg, preferably 1-20 mg/kg. For example, for a person of 60 kg body weight, administration dose for each time can generally be 1 mg-1,800 mg, such as 50 mg-1,200 mg, or 100 mg-900 mg, 150 mg-600 mg or 200 mg-500 mg. Exemplary doses for each administration are, for example, 60 mg, 100 mg, 120 mg, 150 mg, 180 mg, 210 mg, 240 mg, 270 mg, 300 mg, 330 mg, 360 mg, 400 mg, 500 mg, 600 mg, 900 mg, or 1200 mg. The dosing frequency in interval dosing is, for example, once every 3-7 days or once every 1-6 weeks, e.g., once every 3 days, once every 5 days, once a week, once every 10 days, once every 2 weeks, once every 3 weeks, once every 4 weeks, or once every 6 weeks. The specific dosage and frequency of administration should take into account factors such as the route of administration, or the patient's health status, all of which can be determined by a skilled physician according to conventional skills. The mode of administration is not particularly limited, and representative modes of administration include, but not limited to, oral, intratumoral, rectal, parenteral (intravenous, intramuscular or subcutaneous) and topical administration.

In the context of the present application, a "CSF-1/CSF-1R-dependent cancer or tumor" refers to a cancer or tumor in which CSF-1/CSF-1R is highly expressed or highly activated. The high expression or high activation of CSF-1/CSF-1R refers to that the expression level or activation level of CSF-1/CSF-1R in tissues and/or cells of a cancer or tumor, as measured by a person skilled in the art using conventional detection methods in the art (including but not limited to enzyme-linked immunosorbent assay, immunohistochemistry, flow cytometry, western blotting, tissue chip, and gene detection) is 130% or more, preferably 150% or more, more preferably 175% or more, further more preferably 200% or more, even more preferably 250% or more, and most preferably 300% or more of the normal level. The normal level may be the expression or activation level of CSF-1/CSF-1R in the corresponding tissues and/or cells of the normal population, or may be the expression or activation level of CSF-1/CSF-1R in the peri-cancerous tissues and/or cells of the same patient.

In the context of the present application, a "TAMs-enriched tumor" refers to a tumor with abundant TAM infiltration in its tumor tissue. A person skilled in the art would be able to use conventional detection methods in the art (including but not limited to enzyme-linked immunosorbent assay, immunohistochemistry, flow cytometry, western blotting, tissue chip, and gene detection) to detect surface markers of TAMs or count TAMs. Where the expression levels of surface markers of TAMs in the tumor tissue are different from those of the corresponding surface markers in a peri-cancerous tissue, or the TAM count in the tumor tissue is 130% or more, preferably 150% or more, more preferably 175% or more, further more preferably 200% or more, even more preferably 250% or more, and most preferably 300% or more of that in a peri-cancerous tissue, it can be considered that the TAM infiltration is abundant, and the tumor can be regarded as a TAMs-enriched tumor. Surface markers of TAMs include, but not limited to, general TAM surface markers, surface markers of pro-tumor macrophages, and surface markers of tumor-suppressing macrophages. The general TAM surface markers include, but not limited to CD14, CD11 c, CD68 and/or CD11 b, preferably CD68 and/or CD11b. The surface markers of pro-tumor macrophages include, but not limited to, CSF1R, CSF1, CD115, CD206, PPARG, ARG1, CD163, CD301, Dectin-1, PDL2, Fizz1, CD204, PD-L1, Arginase-I, YM1, MGL2, Osteopontin, MMPs or CCR2, preferably CD206. The surface markers of tumor-suppressing macrophages include, but not limited to IL1a, IL1b, IL6, NOS2, TLR2, TLR4, CD80, CD86, MHC-II, CD38, CD40, CD64, HLA-DR(CD74) or CD169, preferably CD86 and/or MHC-II. A difference in the expression level of a surface marker refers to that, where the surface marker is a general TAM surface marker, the expression level of the surface marker in a tumor tissue is 130% or more, preferably 150% or more, and more preferably 200% or more of the expression level of the corresponding surface marker in a peri-cancerous tissue; and where the surface marker is a surface marker (e.g., CD206) of pro-tumor macrophages, the expression level of the surface marker in a tumor tissue is 130% or more, preferably 150% or more, and more preferably 200% or more of the expression level of the corresponding surface marker in a peri-cancerous tissue. Preferably, where the surface marker further comprises a surface marker of tumor-suppressing macrophages (e.g., CD86 and/or MHC-II), the expression level of the surface marker of the tumor-suppressing macrophages in the tumor tissue is 80% or less, and preferably 50% or less of the expression level of the corresponding surface marker in a peri-cancerous tissue.

In the context of the present application, a "tumor insensitive to an immune checkpoint drug" refers to that when the tumor is treated with the immune checkpoint drug at a conventional dose, the tumor inhibition rate is less than 50%. Preferably, the tumor inhibition rate is less than 30%, preferably less than 20%, and more preferably less than 10% when treated with the immune checkpoint drug at a dose around the lower limit of the conventional dosage range. In one embodiment of the present application, the tumor inhibition rate is expressed as the tumor growth inhibition ratio TGI (%), and the calculation formula of TGI (%) is: TGI (%)=$100\times\{1-[(V_{Treated\ Final\ day}-V_{Treated\ Day\ 0})/(V_{Control\ Final\ day}-V_{Control\ Day\ 0})]$, where V is the tumor volume, and is calculated as $V=\frac{1}{2}\times a\times b^2$, where "a" and "b" are the length and width of the tumor, respectively.

In the context of the present application, anti-PD-1 antibodies include, but not limited to, CD279, nivolumab, pembrolizumab, toripalimab, sintilimab, camrelizumab and tislelizumab. Anti-PD-L1 antibodies include, but not limited to, CD274, durvalumab, and atezolizumab.

The values or numeral ranges in the present application may vary within ranges acceptable in the art, e.g., ±10%, or ±9%, or ±8%, or ±7%, or ±6%, or ±5%, or ±4%, or ±3%, or ±2%, or ±1% on the basis of the indicated values or numeral ranges.

As used herein, "subjects", "patients", or "individuals" include all members of the animal community, including, but not limited to, mammals (e.g., mice, rats, cats, monkeys, dogs, horses, and pigs) and humans. Preferably, a subject in the present application is a human. The terms "patient", "subject", and "individual" can be used interchangeably, unless indicated otherwise.

In the context of the present application, pharmaceutically acceptable salts of compounds represented by formulae (A) to (F), in particular a pharmaceutically acceptable salt of Compound I, is not particularly limited, and preferably include hydrochlorides, sulfates, phosphates, nitrates, hydrofluorides, hydrobromides, formates, acetates, picrates, citrates, maleates, methanesulfonates, ethanesulfonates, trifluoromethanesulfonates, and p-toluenesulfonates.

As used herein the term "alkyl group" is preferably an aliphatic alkyl group, which may be a linear alkyl group, a branched alkyl group, a spirocycloalkyl group, a bridged cycloalkyl group, an alkenylalkyl group, an alkynylalkyl group, a cycloalkyl group, a cycloalkenyl group, a cycloalkynyl group, an alkoxyalkyl group, an alkoxyacylalkyl group, a cycloalkylalkyl group, including, but not limited to, methyl, ethyl, n-propyl, isopropyl, n-butyl, isobutyl, tert-butyl, cyclopropyl, cyclobutyl, cyclopentyl, cyclohexyl, allyl, propargyl, cyclobutenyl and cyclohexenyl. The term "$C_1$-$C_8$" is intended to cover groups having 1, 2, 3, 4, 5, 6, 7 or 8 carbon atoms. For example, a "$C_1$-$C_8$ alkyl" refers to an alkyl group having 1, 2, 3, 4, 5, 6, 7 or 8 carbon atoms, and a "$C_2$-$C_{10}$ alkenyl" refers to an alkenyl group having 2, 3, 4, 5, 6, 7, 8, 9 or 10 carbon atoms.

As used herein, a cycloalkyl group may be a saturated or partially unsaturated monocyclic or polycyclic cyclic hydrocarbon group comprising 3 to 20 carbon atoms, preferably 3 to 12 carbon atoms, and more preferably 3 to 10 carbon atoms. Non-limiting examples of monocyclic cycloalkyls include cyclopropyl, cyclobutyl, cyclopentenyl, cyclohexyl, and cyclooctyl. Polycyclic cycloalkyl groups include cycloalkyl groups having spiro, fused and bridged rings.

A heteroaryl group refers to a heteroaromatic system comprising 1 to 4 heteroatoms, and 5 to 14 ring atoms, in which the heteroatoms include oxygen, sulfur, and nitrogen. A heteroaryl is preferably 5-membered or 6-membered group, such as furyl, thienyl, pyridyl, pyrrolyl, N-alkylpyrrolyl, pyrimidinyl, pyrazinyl, imidazolyl, or tetrazolyl. A heteroaryl group can be fused to an aryl, heterocyclyl or cycloalkyl ring, in which the ring, to which the parent structure is attached, is a heteroaryl ring.

Unless otherwise specified, the structural formulae described herein are intended to include all tautomeric, optically isomeric, and stereoisomeric forms (e.g., enantiomers, diastereomers, geometric isomers or conformational isomers), for example, the R and S configurations containing asymmetric centers, (Z) and (E) double bond isomers, and (Z) and (E) conformational isomers. Therefore, single stereochemical isomers as well as a mixture of tautomers or enantiomers, diastereomers or geometric isomers or conformational isomers or tautomers of the compounds are within the scope of the present application.

The term "tautomer" means that structural isomers having different energies can exceed low energy barriers and thus interconvert into each other. For example, proton tautomers (i.e., proton shift) include interconversion by proton migration, such as 1H-indazole with 2H-indazole, 1H-benzo[d]imidazole with 3H-benzo[d]imidazole. Valence tautomers include interconversion by some bond-forming electron recombination.

In vivo and in vitro studies in the present application show the following results (see detailed results of the Examples below).

1 Compound I of the present application significantly inhibits the activity of a CSF1R kinase in vitro.

2 Compound I of the present application is capable of significantly inhibiting the proliferation of CSF1-stimulated mouse-derived macrophages (BMDM) in vitro and inhibiting the phosphorylation of CSF1-stimulated CSF1R and the activation of the downstream signaling molecule AKT in a dose dependent manner, indicating that Compound I is effective in inhibiting the growth of primary macrophages by inhibiting CSF1R.

3 Compound I can significantly inhibit the expression of macrophage marker F4/80 and M2-type macrophage marker CD206 in the tumor issues in nude mouse xenograft tumor model with brain glioma cell line U87MG and nude mouse subcutaneous xenograft tumor model with colorectal cancer cell line HT-29, suggesting that Compound I, as a CSF1R kinase inhibitor, exerts its anti-tumor activity by inhibiting CSF-1-induced macrophage survival and reversing the M2-biased polarization phenotype of macrophages.

4 The results of the in vivo pharmaceutical efficacy tests showed that the growth of xenograft tumor in the nude mouse model with brain glioma cell line U87MG was significantly inhibited by oral administration of Compound I at a dose of 10 mg/kg twice a day for three consecutive weeks. The T/C percentage on Day 21 was 11.91%. The T/C percentage on day 21 was 30.27% in the positive control drug Axitinib group, in which Axitinib was administered at a dose of 40 mg/kg with the same mode of administration. That is, the inhibitory effect of Compound I on tumor growth in this model was significantly superior to that of Axitinib. Oral administration of Compound I at doses of 20 mg/kg, 10 mg/kg, and 5 mg/kg twice a day for three consecutive weeks significantly delayed the growth of the subcutaneous xenograft tumor in the nude mouse model with human colorectal cancer cell line HT-29. The inhibitory effect increased with increasing dose. The T/C percentages on Day 21 were 17.38%, 31.27%, and 42.70%, respectively. The tumors born by the mice receiving the treatment of Compound I at a dose 20 mg/kg almost completely stagnated during three weeks of experimental treatment. This result was significantly superior to that observed for the positive control drug Axitinib (40 mg/kg) group (the T/C percentage on Day 21 was 48.88%).

5 Compound I, when administered alone at a dose of 5 mg/kg, had no significant inhibitory activity against tumors in immunologically healthy mice grafted with mouse astrocytoma DBT. An anti-PD-1 antibody, when administered alone at a dose of 10 mg/kg, had inhibitory effect on tumor growth to a certain extent, but the tumor kept growing slowly. The anti-PD-1 antibody, when administered in combination with Compound I at a dose of 5 mg/kg twice a day, significantly inhibited the tumor growth, in which the tumor volume substantially stayed the same. There was a significant difference in outcome between the combination group and the sole anti-PD-1 antibody group at the end of the experiment. The results showed that an anti-PD-1 antibody, when administered in combination with Compound I, resulted enhanced the anti-tumor efficiency of the anti-PD-1 antibody in the DBT tumor model. Meanwhile, the results of flow cytometry showed that the number of $CD8^+$ T cells in the tumor tissue in the combination group was significantly higher than that in the blank preparation group or the sole anti-PD-1 antibody group, indicating that Compound I can rebuild the tumor suppressive immune microenvironment.

6 In the brain tumor model from U87MG in situ transplantation, the survival time of the mice in each Compound I treatment group was prolonged to various extents. The median survival time of the mice in the 40 mg/kg and 20 mg/kg groups was 58.5 days and 54.0 days, respectively, which were significantly longer than that of the mice in the Axitinib (40 mg/kg) group (41.0 days).

7 The preliminary efficacy results from a clinical trial showed that Compound I had a good therapeutic efficacy for solid tumors, such as brain gliomas, particularly high-grade brain gliomas (specific data are not shown in the present application).

The results of the above studies indicate that Compound I or a pharmaceutically acceptable salt thereof described herein can rebuild a tumor microenvironment, improve a tumor immunosuppressive state, exert an anti-tumor therapeutic effect, and enhance the anti-tumor efficacy of an immune checkpoint drug, and therefore has a good clinical application prospect.

BRIEF DESCRIPTION OF THE SEVERAL VIEWS OF THE DRAWING(S)

DETAILED DESCRIPTION OF THE INVENTION

Figure 1:
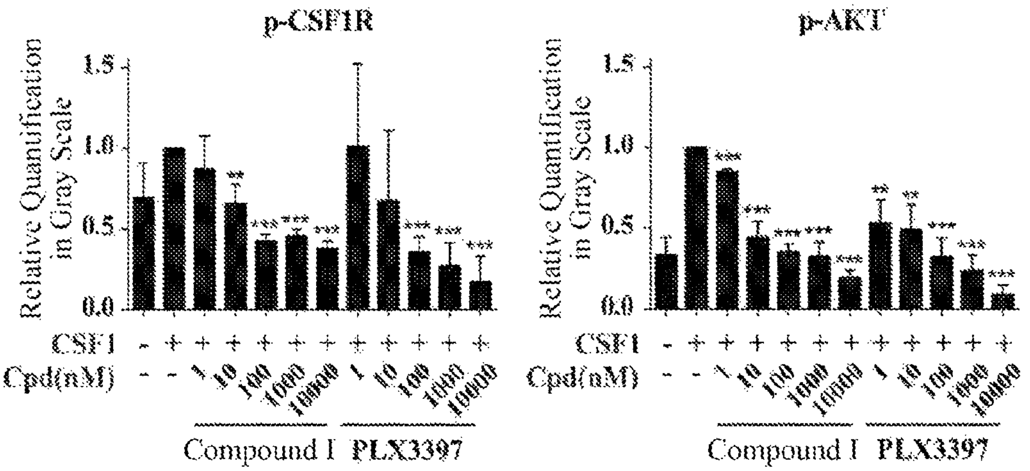
FIG. 1 shows the effect of Compound I and the control compound PLX3397 on CSF1R phosphorylation and the downstream signaling pathway in BMDM.

The inventions are further illustrated below in reference to particular examples. It should be understood that these examples are merely illustrative of the present application and are not intended to limit the scope of the present application. The experimental methods without specifying their protocols in the following examples are generally carried out according to conventional protocols, or according to protocols recommended by manufacturers.

Source or Preparation of Experimental Materials

Compound I was prepared by SHANGHAI RUNSHI MEDICAL TECHNOLOGY CO., LTD.

The positive control compounds, reagent and raw materials used in the Examples were all commercially purchased or self-prepared.

In in vitro tests, Compound I and the positive control compounds were weighed and dissolved in DMSO to $10^{-2}$ mol/L, and then diluted to desired concentrations immediately prior to use.

In in vivo tests, Compound I was prepared into a formulation as described in below table.

| Raw Materials | Amount |
|---|---|
| Compound I | 60 mg |
| medium chain triglyceride | 1 ml |
| polyoxyethylene 40 hydrogenated castor oil | 1.5 ml |
| diethylene glycol monoethyl ether | 2.5 ml |
| oleic acid | 1 ml |
| ethanol:ethyl acetate (1:1) as latent solvent | 15-20 ml |

Example 1

Effect of Compound I on CSF1R Kinase Activity

1. ELISA Assay

The enzyme reaction substrate poly(Glu, Tyr)$_{4:1}$ was diluted to 20 μg/mL with potassium-free PBS (10 mM sodium phosphate buffer, 150 mM NaCl, pH7.2-7.4). Plates were coated with the dilution, allowed to incubate at 37° C. for 12-16 h, washed with T-PBS (0.1% Tween-20 in potassium-free PBS), and dried for later use. An ATP solution (final concentration of 5 μM) diluted with a reaction buffer (50 mM HEPES pH 7.4, 50 mM $MgCl_2$, 0.5 mM $MnCl_2$, 0.2 mM $Na_3VO_4$, 1 mM DTT), a test compound or solvent control, and a recombinant CSF1R kinase were added sequentially to individual wells to initiate the reaction. After reaction at 37° C. for 1 hour, the plates were washed with T-PBS, and the antibody PY99 dilution was added. The plates were incubated on a shaker at 37° C. for 0.5 h, and then washed with T-PBS. A horseradish peroxidase-labeled goat anti-mouse secondary antibody dilution was added, and the plates were incubated at 37° C. for 0.5 h. After the plates were washed, an OPD developing solution (diluted with 0.1 M citric acid-sodium citrate buffer (pH=5.4) containing 0.03% $H_2O_2$) was added at 2 mg/mL and the plates were allowed to react in the dark at 25° C. for 1 to 10 minutes. Finally, 2 M $H_2SO_4$ was added to stop the reaction. The plates were read with an adjustable wavelength microplate reader at a wavelength of 490 nm. The inhibition rate was calculated as follows.

$$\text{Inhibition Rate \%} = (1-\frac{\text{Compound } OD \text{ value - Enzyme-free control } OD \text{ value})}{\text{Solvent } OD \text{ value - Enzyme-free control } OD \text{ value} \times 100\%}$$

The $IC_{50}$ values were calculated by a four-parameter regression program in the software embedded in the microplate reader.

2. Results

Compound I was shown to have a significant inhibitory effect on the activity of an important target, CSF1R kinase, in tumor-associated macrophages with an $IC_{50}$ of 19.3±3.4 nM, which was comparable to the $IC_{50}$ of a marketed drug Pexidartinib (PLX3397). This suggests that Compound I has the potential to rebuild tumor microenvironments and antagonize tumors.

TABLE 1

Inhibition of CSF1R Kinase Activity by Compound I

| Compound | $IC_{50}$ (nM) |
|---|---|
| Compound I | 19.3 ± 3.4 |
| PLX3397 | 14.4 ± 1.3 |

Example 2

Effect of Compound I on Survival of Primary Macrophages and Intracellular CSF1R Signal Pathway

1. Methods 1.1 Isolation and Culture of Bone Marrow-Derived Macrophages (BMDM)

Mice (BALB/c) were subjected to euthanasia and then immersed in 75% alcohol for 3-5 min. The tibias and femurs of the mice were removed with ophthalmic forceps and ophthalmic clips on an ultraclean table. The tibial and femoral joints were cut off and bone marrow cells were washed out with a sterile buffer. Bone marrow cells were filtered with a 70 m nylon membrane. The filtrate was centrifuged and the supernatant was discarded. An erythrocyte lysate was added to the pellets, which were allowed to incubate for 3-4 min. Then, a sterile buffer was added to stop the lysis reaction. The reactant was centrifuged and the supernatant was discarded, thereby yielding bone marrow cell pellets. The cells were cultured in 1640 medium (supplemented with FBS and 10 ng/mL of CSF1) for 5 to 7 days and identified as macrophages by flow cytometry.

1.2 Cell Proliferation Inhibition Assay

CCK8 cell counting kits were used in this assay. Bone marrow-derived macrophages, after induction by CSF1 for 5 to 7 days, were seeded into 96-well culture plates and allowed to incubate overnight. Then, the cells were exposed to compounds at various concentrations for 72 h. A blank control group was set. 10 μL of CCK8 reagent was added to each well and the places were placed in an incubator for 4 to 12 h. The plates were read with a microplate reader at a wavelength of 450 nm. The inhibition rate of a compound on cell growth was calculated using the following equation:

$$\text{Inhibition rate } \% = (\text{blank control OD value} - \text{test group OD value}) / \text{blank control OD value} \times 100\%$$

$IC_{50}$ values were calculated using a four-parameter program. Each experiment was independently repeated for three times.

1.3 Western Blot

Bone marrow-derived macrophages, after induction by CSF1 for 5 to 7 days, were centrifuged to remove the previous medium. 2 mL of a serum-free medium was added. After the cells were starved for 6 h, Compound I and the positive drug PLX3397 were added at different concentrations to react for 2 h. CSF1 factor was added at a final concentration of 50 ng/mL for stimulation for 15 minutes. The culture medium was discarded, and cells were washed three times with pre-cooled PBS. Then, the cells were lysed by adding 1×SDS gel loading buffer. The cell lysates were heated in a boiling water bath for 15 min, and then stored at −20° C.

A protein sample as described above was subjected to SDS-PAGE electrophoresis. Then, the protein was transferred to a nitrocellulose membrane using a semi-dry electrotransfer system. The nitrocellulose membrane was placed in a blocking solution (5% skim milk in TBS-T) and incubated for 2 h at room temperature. Then, the membrane was allowed to react with a primary antibody overnight at 4° C. After the membrane was washed with TBS-T for three times with 15 min each time, the membrane was allowed to react in a secondary antibody dilution at room temperature for 1-2 h. After the membrane was washed with TBS-T for three times with 15 min each time, the membrane was developed with a developing agent.

2. Results 2.1 Proliferation Inhibitory Effect of Compound I on BMDM

The in vitro proliferation inhibitory activity of Compound I against BMDM cells was measured using the CCK8 kit. The $IC_{50}$ values are shown in Table 2. Compound I significantly inhibited CSF1-stimulated proliferation of BMDM cells with an average $IC_{50}$ of 0.093+0.024 μM. The inhibitory activity was slightly less than that of the positive drug PLX3397 (0.030±0.009 μM).

TABLE 2

$IC_{50}$ (μM) of Compound I in Inhibiting Proliferation of BMDM Cells

| Compound | $IC_{50}$ (μM) |
|---|---|
| Compound I | 0.093 ± 0.024 |
| PLX3397 | 0.030 ± 0.009 |

2.2 Detection of Target Inhibitory Activity of Compound I Against BMDM

The inhibitory effect of Compound I on CSF1R and its signaling pathway in mouse primary macrophages was detected by immunoblotting assays. Each experiment was independently repeated three times and all experimental results were quantified. The results are shown in FIG. 1 (experimental data was subjected to t-test analysis statistics,  represents $p<0.01$ as compared with the blank control group, * represents $p<0.001$ as compared with the blank control group). CSF1 stimulation activated CSF1R, characterized by upregulation of phosphorylated CSF1R (p-CSF1R) expression and activation of downstream signaling molecule AKT (increased level of phosphorylated AKT (p-AKT)). After treatment with Compound I, CSF1 stimulated phosphorylation levels of CSF1R and AKT were inhibited in a dose-dependent manner, with 57.3% inhibition of CSF1R phosphorylation and 64.4% inhibition of AKT phosphorylation at the concentration of 100 nM. The inhibitory activity of Compound I was comparable to that of the positive drug PLX3397.

Example 3

Inhibition of Growth of Human Glioma U87MG Xenografts in Nude Mice by Compound I

1. Animals

BALB/c nude female mice of 3-4 weeks old were used, and were provided by SHANGHAI INSTITUTE OF MATERIA MEDICA, CHINESE ACADEMY OF SCIENCES.

2. Methods

Human glioma U87MG cells were subcutaneously inoculated into the right axillary fossa of a nude mouse ($5\times10^6$ cells/mouse). After a xenograft was formed, the tumor was transferred to a nude mouse for 1 passage.

Tumor tissues at the vigorous growth stage were removed and cut into pieces of approximately 1.5 $mm^3$. The tumor fragments were inoculated subcutaneously into the right axillary fossa of nude mice under aseptic conditions. The diameters of the subcutaneous xenografts in nude mice were measured with a vernier caliper. The animals were randomly grouped after the xenografts reached an average volume of about 90 $mm^3$. Compound I was administered orally at doses of 40 mg/kg, 20 mg/kg and 10 mg/kg twice a day for 21 consecutive days. An equal volume of a blank preparation was administered orally twice a day for 21 consecutive days. The positive control drug Axitinib was administered orally at a dose of 40 mg/kg group twice a day for 21 consecutive days. An equal volume of water for injection was administered to the animals in the solvent group. Throughout the experiment, the diameters of the xenografts were measured twice a week and the mice were weighed at the same time. The tumor volume (TV) was calculated as $TV=\frac{1}{2}\times a\times b^2$, where "a" and "b" denote the length and width of a tumor, respectively. The relative tumor volume (RTV) was calculated from the measurement results with the calculation formula $RTV=V_t/V_0$, in which $V_0$ is the tumor volume measured upon administration after grouping (i.e., D0) and $V_t$ is the tumor volume from each measurement. The evaluation index of anti-tumor activity is the relative tumor proliferation rate T/C (%), which is calculated as T/C $(\%)=(T_{RTV}/C_{RTV})\times100\%$, in which $T_{RTV}$ denotes the RTV from the treatment group and $C_{RTV}$ denotes the RTV from solvent group.

3. Results

The results are shown in Table 3. In the blank preparation group, a preparation identical to that of the Compound I formulation (only without Compound I) was administered by gavage twice a day for 21 consecutive days. This did not cause a significant effect on the growth of human glioma U87MG subcutaneous xenografts in nude mice. The T/C percentage on Day 21 was 79.86%.

The test substance Compound I, which was orally administered at doses of 40 mg/kg, 20 mg/kg, and 10 mg/kg twice a day for three consecutive weeks, significantly inhibited the growth of human glioma U87MG subcutaneous xenografts in nude mice. The T/C percentages on Day 21 were 9.77%, 8.14%, and 11.91%, respectively.

The positive control drug Axitinib, which was orally administered at a dose of 40 mg/kg twice a day using the same dosing regimen for 21 consecutive days, significantly inhibited the growth of human glioma U87MG subcutaneous xenografts in nude mice. The T/C percentage on Day 21 was 30.27%.

In this model, the inhibitory effect of Compound I (10 mg/kg) on tumor growth was superior to that of Axitinib (40 mg/kg).

In the experiments, mice in each group were in good condition.

2. Methods

Human colorectal cancer HT-29 cells were subcutaneously inoculated into the right axillary fossa of a nude mouse ($5\times10^6$ cells/mouse). After a xenograft was formed, the tumor was transferred to a nude mouse for 1 passage.

Tumor tissues at the vigorous growth stage were removed and cut into pieces of approximately 1.5 $mm^3$. The tumor fragments were inoculated subcutaneously into the right axillary fossa of nude mice under aseptic conditions. The diameters of the subcutaneous xenografts in nude mice were measured with a vernier caliper. The animals were randomly grouped after the xenografts reached an average volume of about 120 $mm^3$. Compound I was administered orally at doses of 20 mg/kg, 10 mg/kg and 5 mg/kg twice a day for 21 consecutive days. An equal volume of a blank preparation was administered orally twice a day for 21 consecutive days. The positive control drug Axitinib was administered orally at a dose of 40 mg/kg group twice a day for 21 consecutive days. An equal volume of water for injection was administered to the animals in the solvent group. Throughout the experiment, the diameters of the xenografts were measured twice a week and the mice were weighed at the same time. The tumor volume (TV) was calculated as $TV=\frac{1}{2}\times a\times b^2$, where "a" and "b" denote the length and width of a tumor, respectively. The relative tumor volume (RTV) was calculated from the measurement results with the calculation formula $RTV=V_t/V_0$, in which $V_0$ is the tumor volume measured upon administration after grouping (i.e., D0) and $V_t$ is the tumor volume from each measurement. The evaluation index of anti-tumor activity is the relative tumor proliferation rate T/C (%), which is calculated as T/C $(\%)=(T_{RTV}/C_{RTV})\times100\%$, in which $T_{RTV}$ denotes the RTV from the treatment group and $C_{RTV}$ denotes the RTV from solvent group.

TABLE 3

Therapeutic effects of Compound I on human glioma U87MG subcutaneous xenografts in nude mice

| Groups | Dosage & Mode of Administration | | Animals D 0 | Animals D 21 | Body Weight (g) D 0 | Body Weight (g) D 21 | TV ($mm^3$, mean ± SD) D 0 | TV ($mm^3$, mean ± SD) D 21 | RTV (mean ± SD) | T/C (%) |
|---|---|---|---|---|---|---|---|---|---|---|
| Solvent | 0.2 mL/20 g bid × 21 | po | 6 | 6 | 16.6 | 20.4 | 86 ± 21 | 2402 ± 517 | 29.99 ± 11.14 | |
| Blank preparation | 0.2 mL/20 g bid × 21 | po | 6 | 6 | 15.9 | 19.7 | 91 ± 22 | 1996 ± 886 | 23.95 ± 11.79 | 79.86 |
| Axitinib | 40 mg/kg bid × 21 | po | 6 | 6 | 16.0 | 18.0 | 88 ± 17 | 795 ± 478 | 9.08 ± 5.66* | 30.27 |
| Compound I | 40 mg/kg bid × 21 | po | 6 | 6 | 17.0 | 17.6 | 87 ± 15 | 251 ± 37 | 2.93 ± 0.50** | 9.77 |
| | 20 mg/kg bid × 21 | po | 6 | 6 | 16.7 | 16.9 | 87 ± 17 | 200 ± 100 | 2.44 ± 1.58** | 8.14 |
| | 10 mg/kg bid × 21 | po | 6 | 6 | 15.7 | 17.3 | 87 ± 17 | 302 ± 72 | 3.57 ± 1.06** | 11.91 |

The experimental data were subjected to t-test statistic analysis,
*$p < 0.01$,
**$p < 0.001$ Example 4

Inhibition of Growth of Human Colorectal Cancer HT-29 Xenografts in Nude Mice by Compound I 1. Animals BALB/c female nude mice of 6 weeks old were used, and were provided by Shanghai Lingchang Biotechnology Co., Ltd.

3. Results

The results are shown in Table 4. In the blank preparation group, the blank preparation was administered by gavage twice a day for 21 consecutive days. This did not cause a significant effect on the growth of human colorectal cancer HT-29 subcutaneous xenografts in nude mice. The T/C percentage on Day 21 was 87.68%.

The test substance Compound I, which was orally administered at doses of 20 mg/kg, 10 mg/kg, and 5 mg/kg under the same treatment regimen, significantly inhibited the growth of the xenografts. The inhibitory effect increased with increasing dose. The T/C percentages on Day 21 were 17.38%, 31.27% and 42.70%, respectively. The tumors born by the mice receiving the treatment of Compound I at a dose 20 mg/kg almost completely stagnated during three weeks of experimental treatment.

The positive control drug Axitinib, which was orally administered at a dose of 40 mg/kg twice a day for 21 consecutive days, partially inhibited the growth of human colorectal cancer HT-29 subcutaneous xenografts in nude mice. The T/C percentage on Day 21 was 48.88%, which was comparable to that of Compound I at a dose of 5 mg/kg.

blank preparation group, and denotes p<0.001 as compared with the blank preparation group.

For detecting the changes in the macrophage marker F4/80 and M2-type macrophage marker CD206 in the HT-29 tumor tissues, quantitative analysis (solvent: n=12, blank preparation: n=6, Compound I (5 mg/kg): n=6, Compound I (10 mg/kg): n=6, Compound I (20 mg/kg): n=6, Axitinib: n=6) was performed on all sections and the experimental data were analyzed for significant differences using the t-test. * denotes p<0.05 as compared with the blank preparation group, ** denotes p<0.01 as compared with the blank preparation group, and denotes p<0.001 as compared with the blank preparation group.

TABLE 4

Therapeutic effects of Compound I on human colorectal cancer HT-29 subcutaneous xenografts in nude mice

| Groups | Dosage & Mode of Administration | | Animals D 0 | Animals D 21 | Body Weight (g) D 0 | Body Weight (g) D 21 | TV (mm3, mean ± SD) D 0 | TV (mm3, mean ± SD) D 21 | RTV (mean ± SD) | T/C (%) |
|---|---|---|---|---|---|---|---|---|---|---|
| Solvent | 0.2 mL/20 g bid × 21 | po | 12 | 12 | 19.9 | 18.8 | 119 ± 34 | 992 ± 329 | 8.80 ± 3.47 | |
| Blank preparation | 0.2 mL/20 g bid × 21 | po | 6 | 6 | 19.7 | 18.1 | 120 ± 29 | 918 ± 223 | 7.71 ± 1.16 | 87.68 |
| Axitinib | 40 mg/kg bid × 21 | po | 6 | 6 | 19.1 | 17.5 | 123 ± 35 | 505 ± 202 | 4.30 ± 1.82* | 48.88 |
| Compound I | 20 mg/kg bid × 21 | po | 6 | 6 | 20.1 | 18.2 | 121 ± 35 | 188 ± 69 | 1.53 ± 0.25** | 17.38 |
| | 10 mg/kg bid × 21 | po | 6 | 6 | 19.8 | 18.1 | 120 ± 33 | 336 ± 173 | 2.75 ± 1.04** | 31.27 |
| | 5 mg/kg bid × 21 | po | 6 | 6 | 19.7 | 18.6 | 113 ± 28 | 427 ± 157 | 3.76 ± 0.87* | 42.70 |

The experimental data were subjected to t-test statistic analysis,
*p < 0.01,
**p < 0.001

Example 5

Effect of Compound I on Macrophage-Associated Markers (F4/80, CD206) in Human Glioma U87MG Xenografts in Nude Mice and Human Colorectal Cancer HT-29 Xenografts in Nude Mice

1. Methods

At the end of the in vivo experiments, U87MG and HT-29 xenografts in nude mice were removed and fixed with 400 paraformaldehyde to prepare paraffin sections.

Expression of individual proteins was assessed using multiplicative quick score method (MQS). This evaluation method takes into account both the staining intensity and the staining range. The method estimates the proportion of positive cells and gives a range score from 1 to 6 (1=1%-4%; 2=5%-19%; 3=20%-39%; 4=40%-59%; 5=60%-79%; 6=80%-100%). The average intensity score of positive stained cells was 0 to 3 (0=no staining; 1=weak staining; 2=moderate staining; 3=strong staining). The total score a (minimum 0 and maximum 18) is then calculated by multiplying the range score by the intensity score.

For detecting the changes in the macrophage marker F4/80 and M2-type macrophage marker CD206 in the U87MG tumor tissues, quantitative analysis (solvent: n=6, blank preparation: n=6, Compound I (10 mg/kg): n=6, Compound I (20 mg/kg): n=6, Compound I (40 mg/kg): n=6, Axitinib: n=4) was performed on all sections and the experimental data were analyzed for significant differences using the t-test. * denotes p<0.05 as compared with the blank preparation group, ** denotes p<0.01 as compared with the blank preparation group, and denotes p<0.001 as compared with the blank preparation group.

2. Results

Figure 2:
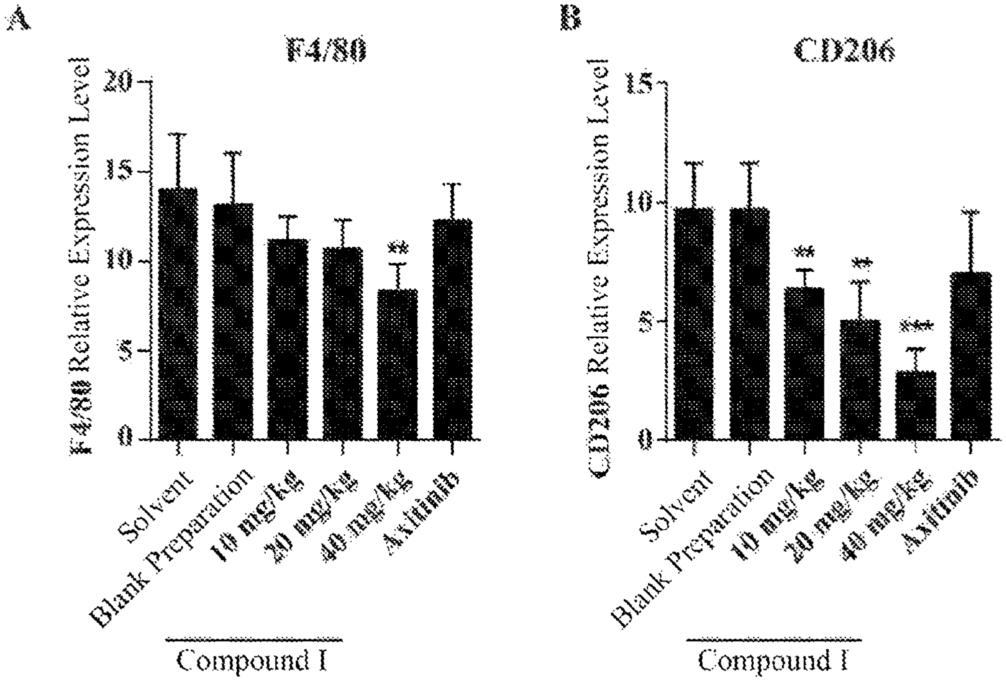
FIG. 2 shows the inhibitory effect of Compound I on the number and polarity of macrophages in nude mice U87MG xenografts, in which panel A shows the results from immunohistochemical quantitative statistical analysis of F4/80, and panel B shows the results from immunohistochemical quantitative statistical analysis of CD206.

2.1 Changes in Macrophage Marker F4/80 and M2-Type Macrophage Marker CD206 in U87MG Tumor Tissues Compound I (40 mg/kg) significantly reduced the expression of F4/80 in macrophages as compared with the blank preparation group, indicating a decrease in the number of macrophages in the tumor tissue (panel A in FIG. 2). In addition, Compound I significantly inhibited the expression of the M2-type macrophage marker CD206 in a dose-dependent manner (panel B in FIG. 2). The inhibition rates were significant, with 34.48% for the 10 mg/kg dose group and 70.69% for the 40 mg/kg dose group. In contrast, Axitinib (40 mg/kg) had no significant effect on the expression of individual macrophage-associated markers, which was consistent with the fact that Axitinib did not inhibit the CSF1R kinase activity and thus did not affect macrophage function. The above results suggest that Compound I, as a CSF1R kinase inhibitor, exerts its anti-tumor activity by inhibiting CSF-1-induced macrophage survival and reversing the M2-biased polarization phenotype of macrophages.

Figure 3:
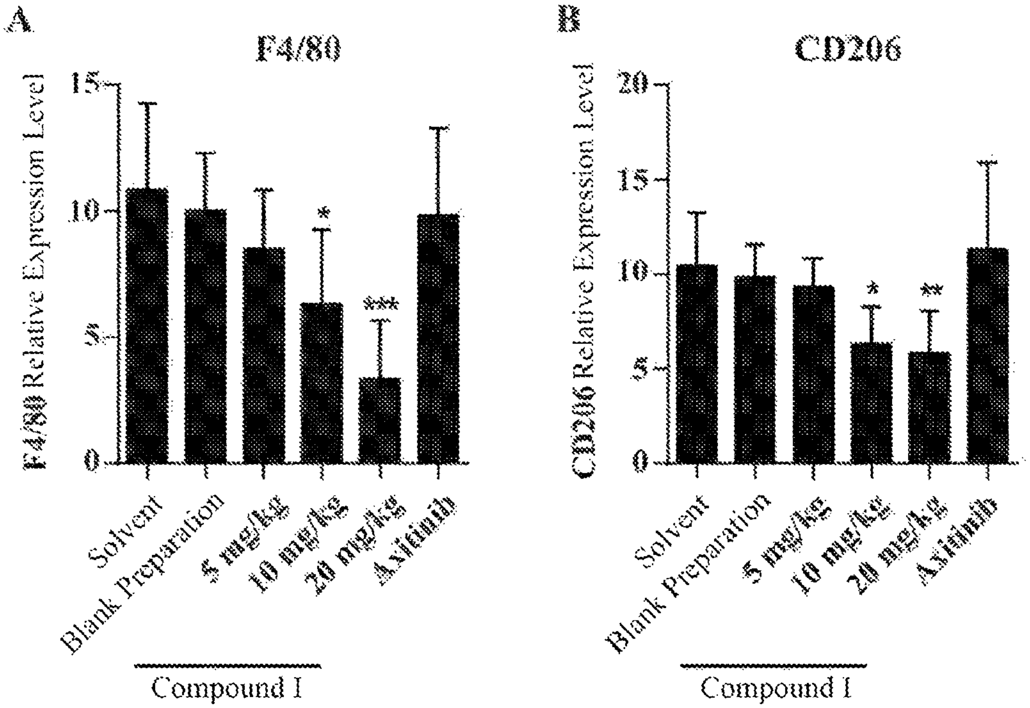
FIG. 3 shows the inhibitory effect of Compound I on the number and polarity of macrophages in nude mice HT-29 xenografts, in which panel A shows the results from immunohistochemical quantitative statistical analysis of F4/80, and panel B shows the results from immunohistochemical quantitative statistical analysis of CD206.

2.2 Changes in Macrophage Marker F4/80 and M2-Type Macrophage Marker CD206 in HT-29 Tumor Tissues In the HT-29 xenograft model in nude mice, Compound I inhibited the expression of F4/80 and CD206 in a dose-dependent manner. There is a highly significant difference in inhibitory activity between the blank preparation and Compound I at a dose of 20 mg/kg. In contrast, the positive drug Axitinib had no inhibitory activity on the expression of F4/80 and CD206, as shown in panels A and B in FIG. 3.

Example 6

Enhancement of Immune Checkpoint Drug's Anti-Tumor Efficacy by Compound I

1. Methods

Mouse astrocytoma DBT cell suspensions were injected subcutaneously into the right axillary fossa of BALB/c mice under aseptic conditions. The diameters of the subcutaneous xenografts in nude mice were measured with a vernier caliper. The animals were randomly grouped after the xenografts reached an average volume of 100 to 200 $mm^3$. Compound I was administered orally at a dose of 5 mg/kg (alone or in combination with an anti-PD-1 antibody) twice a day for 28 consecutive days. An anti-PD-1 antibody (Bio X Cell, InVivoMAb anti-mouse PD-1 (CD279) (cat. No. BE0146)) was administered intraperitoneally at a dose of 10 mg/kg (alone or in combination with Compound I) once every three days for 28 consecutive days. Throughout the experiment, the diameters of the xenografts were measured twice a week and the mice were weighed at the same time. The tumor volume (TV) was calculated as $TV=\frac{1}{2}\times a\times b^2$ where "a" and "b" denote the length and width of a tumor, respectively. The relative tumor volume (RTV) was calculated from the measurement results with the calculation formula $RTV=V_t/V_0$, in which $V_0$ is the tumor volume measured upon administration after grouping (i.e., D0) and $V_t$ is the tumor volume from each measurement.

At the end of the experiment, fresh tumors were removed and cut into pieces. The tumor tissue fragments were resuspended with 2.5 mL of an enzyme solution, and digested at 37° C. in a shaker. After incubation for 30 to 60 minutes, cell suspensions were obtained by filtration with a 70 μM filter. An erythrocyte lysing buffer was used to treat the cells for 10 minutes. Then, the cells were centrifuged at 300 g for 5 minutes, resuspended in PBS and counted. Next, antibody staining-based flow cytometry was performed. The test cells were washed twice with PBS, then resuspended with 100 μL of PBS and stained with 0.5 μL of fluorescent antibody FVS510 at 4° C. in the dark for 30 minutes. Then, the sample was washed twice with 1 mL of loading buffer (#130-091-221-1, Miltenyi) and centrifuged at 4° C. at 300 g for 5 minutes. A blocking antibody dilution (1 μL of murine anti-CD16/32 in 200 μL of buffer described above) was prepared. Each sample was blocked with 200 μL of blocking antibody dilution, and then 1 μL of CD45 and CD8 antibody was added and allowed to incubate at 4° C. for 30 minutes. At this step, a single staining control was set. The single staining control was similarly washed twice with 1 mL of loading buffer, and during each washing, the sample was centrifuged at 4° C. at 300 g for 5 minutes. Finally, each sample was resuspended with 300 μL of loading buffer, and the flow cytometry analysis was performed on a Fortessa flow cytometer (BD).

For all dose groups, n=9. The experimental data were analyzed for significant differences using the t-test. "ns" denotes no significant differences as compared with the blank preparation group, *denotes $p<0.05$ as compared with the blank preparation group, and ** denotes $p<0.01$ as compared with the blank preparation group.

2. Results

Figure 4:
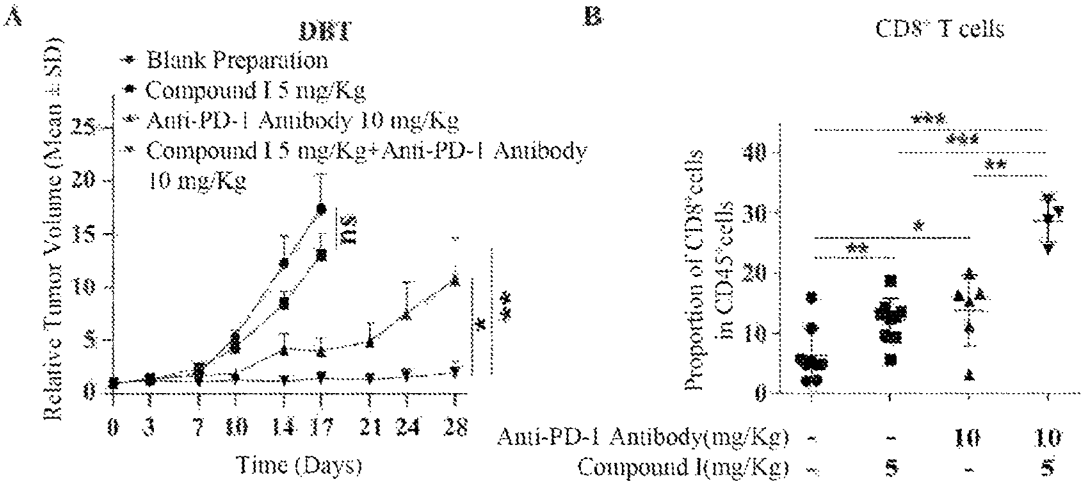
FIG. 4 shows the sensitizing effect of Compound I on immune checkpoint drugs, in which panel A shows the inhibitory effect of the combination of Compound I and an anti-PD-1 antibody on the growth of mouse subcutaneous xenografts of glioma DBT, and panel B shows the effect of the combination of Compound I and an anti-PD-1 antibody on the content of CD8+ T cells in tumor tissues.

Compound I, when administered alone at a dose of 5 mg/kg, had no significant inhibitory activity on in vivo growth of DBT tumors. The anti-PD-1 antibody, when administered alone at a dose of 10 mg/kg, had inhibitory effect on tumor growth to a certain extent, but the tumor kept growing slowly. The anti-PD-1 antibody, when administered in combination with Compound I at a dose of 5 mg/kg twice a day, significantly inhibited the tumor growth, in which the tumor volume substantially stayed the same. At the end of the experiment, the tumor volume of the combination group was 19.89% of that of the anti-PD-1 antibody monotherapy group. The results showed that an anti-PD-1 antibody, when administered in combination with Compound I, resulted in enhanced anti-tumor efficiency of the anti-PD-1 antibody in the DBT tumor model. Meanwhile, the results of flow cytometry showed that the number of $CD8^+$ T cells in the tumor tissue in the combination group was significantly higher than that in the blank preparation group or the sole anti-PD-1 antibody group, indicating that Compound I can rebuild the tumor suppressive immune microenvironment. Detailed results are shown in panels A and B in FIG. 4.

Example 7

Effect of Compound I on Survival in Brain Inoculation of Human Glioma U87MG Mice 1. Animals BALB/cA nude male mice of 7-8 weeks old were used and were purchased from Shanghai Jihui Experimental Animal Breeding Co., Ltd.

2. Methods

After the nude mice were injected intraperitoneally with Sutai 50 (50 mg/kg) for anesthesia, the nude mice were placed at ventricumbent position in a brain stereotaxie apparatus to fix their heads. A cut was longitudinally made at the intersection of the medial canthal line and the sagittal midline of the head, so as to expose cranium. A hole was drilled on the right side of the anterior fontanel level by 2 mm and 0.5 mm anteriorly. U87MG cells ($5\times10^5$ cells/mouse) were seeded into the right caudate nucleus of the brain in nude mice. The incisions were sutured with sterile medical sutures. The animals were kept warm until awakened. 7 days after the implantation, mice were randomly grouped (implantation day as Day 0). Treatment with different compounds was initiated on Day 8. Compound I was administered orally at a dose of 40 mg/kg or 20 mg/kg twice a day until the mice naturally died. The positive control drug Axitinib was administered orally at a dose of 40 mg/kg group twice a day until the mice naturally died. An equal volume of water for injection was administered to the mice in the solvent group (Vehicle). An equal volume of the blank preparation was administered to the mice in the blank preparation group. Throughout the experiment, mice were weighed twice a week. During the experiment, mouse deaths were recorded and survival rates were calculated. The experimental data were analyzed by Log-rank, with $p<0.05$ being a significant difference.

3. Results

Figure 5:
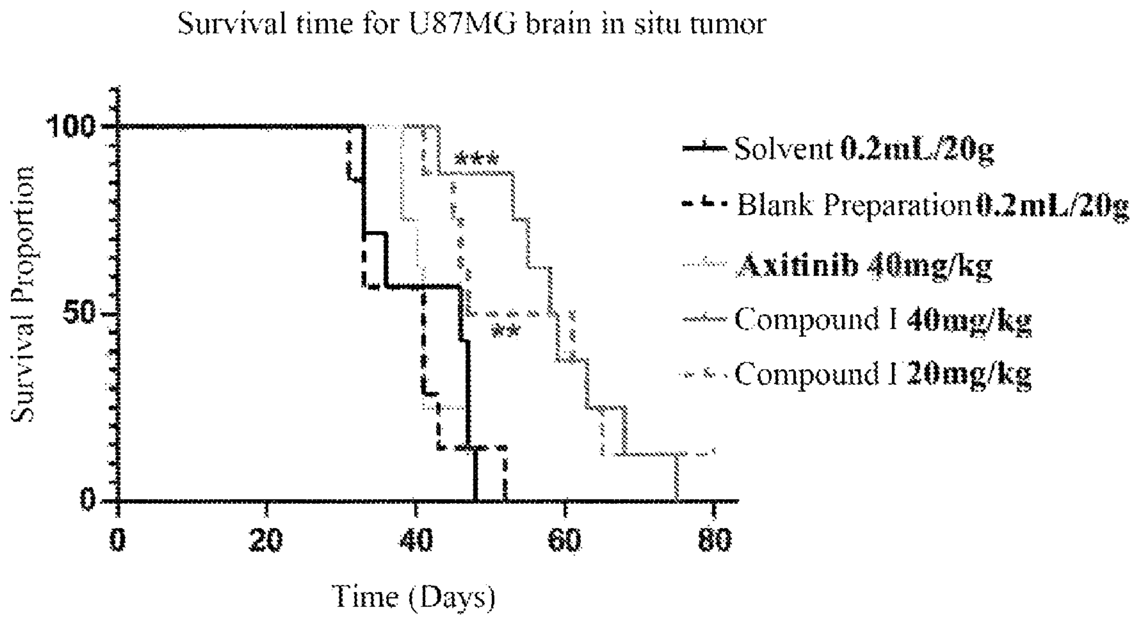
FIG. 5 shows the effect of Compound I on survival of mice bearing in situ U87MG brain tumors.

The experimental results are shown in Table 5 and FIG. 5. Treatment in individual groups started on Day 8 from the implantation. Mice in the solvent group started die from Day 27 and all mice in this group died by Day 48 with a median survival time of 46 days. Mice in the blank preparation group began to die on Day 31 and the last mouse in the group died on Day 52, with a median survival time of 41 days. There is no significant difference between the solvent group and the blank preparation group.

Tumor-bearing mice in the positive control drug Axitinib (40 mg/kg) group successively died during the experimental treatment. The first died animal in the group occurs on Day 28, and all mice in the group died on Day 48. The median survival time of the group was 41 days. There is no significant difference between the solvent group and the positive control drug Axitinib (40 mg/kg) group.

Similar to the anti-tumor effect exhibited by Compound I on the U87MG subcutaneous xenograft models in nude mice, the survival time for different Compound I treatment groups was extended to varying degrees in the U87MG brain in situ transplantation model in nude mice. Mice in the Compound I (40 mg/kg) treatment group began to die on Day 43, and the last mouse in this group died on Day 75. The median survival time was 58.5 days, which was significantly longer than that in the solvent group, the blank preparation group, or the Axitinib group. Administration of Compound I at a dose of 20 mg/kg also prolonged the survival time of the mice with a median survival time of 54 days.

TABLE 5

Effect of Compound I Treatment on Median Survival Time of Human Glioma U87MG brain in situ transplantation in Nude Mice

| Test substance | Dose (mg/kg) | Animals (start/end) | Median survival time, MST (days) | ILS (%) |
|---|---|---|---|---|
| Solvent | 0.2 mL/20 g | 7/0 | 46.0 | |
| Blank preparation | 0.2 mL/20 g | 7/0 | 41.0 | −10.87 |
| Axitinib | 40 mg/kg | 8/0 | 41.0 | −10.87 |
| Compound I | 40 mg/kg | 8/0 | 58.5 | 27.17 |
| | 20 mg/kg | 8/1 | 54.0 | 17.39 |

Note:
ILS: Increase in Life Span = (treatment group MST/solvent group MST-1) × 100%

The full names of the English abbreviations used in the present application are as follows:

CSF1R: Colony-stimulating factor 1 receptor
CSF-1: Colony-stimulating factor 1
TAMs: Tumor-associated macrophages
Treg: Regulatory T cells
DC: Dendritic cells
TGCT: Tenosynovial giant cell tumor
VEGF: Vascular endothelial growth factor
VEGFR: Vascular endothelial growth factor receptor
DBT: mouse braina stroglioma cells
AKT: Protein kinase B, PKB
DMSO: Dimethylsulfoxide
ELISA: Enzyme linked immunosorbent assay
Poly (Glu, Tyr)4:1: Polyglutamate-tyrosine peptide fragment (4:1)
HEPES: 4-Hydroxyethylpiperazine ethanesulfonic acid
DTT: DL-Dithiothreitol
ATP: Adenosine triphosphate
PY99: Anti-phosphorylated tyrosine monoclonal antibody
OPD: O-Phenylenediamine
OD: Optical density
BALB/c: An immunodeficient mouse subline
FBS: Fetal bovine serum
SDS: Sodium dodecyl sulfate
SDS-PAGE: Sodium dodecyl sulfate polyacrylamide gel electrophoresis
TBS-T: Triethanolamine buffered saline solution (containing 0.05% Tween-20)
PBMC: Peripheral blood mononuclear cell
BMDM: Bone marrow-derived macrophages
PD-1: Programmed cell death protein 1
PD-L1: Programmed cell death 1 ligand 1
FMO: Fluorescence Minus One
Log-rank: Log rank
PBS: Phosphate buffer saline
FVS510: Fixable viability stain 510, a dye for identifying cellular viability

The invention claimed is:

1. A method of treating or inhibiting a tumor, comprising administering a therapeutically effective amount of a compound represented by formula (I) or a pharmaceutically acceptable salt thereof in combination with an immune checkpoint drug to a subject in need of treatment or inhibition of the tumor, wherein the immune checkpoint drug is an anti-PD-1 antibody or an anti-PD-L1 antibody:

(I)

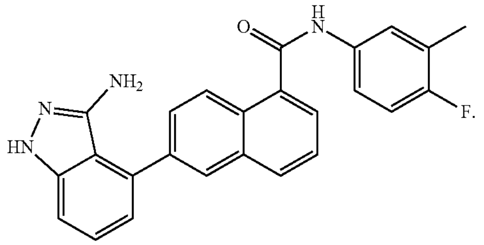

2. The method of claim 1, wherein the tumor is a glioma, a metastatic brain tumor, or a colorectal cancer.

* * * * *